(12) United States Patent
Turner et al.

(10) Patent No.: US 6,500,164 B1
(45) Date of Patent: Dec. 31, 2002

(54) SUCTION DEVICE

(76) Inventors: Janet C. Turner, 5580 NW. 38 Ter., Coconut Creek, FL (US) 33073; Janet M. Collins, 1926 N. 38 Ave., Hollywood, FL (US) 33021

( * ) Notice: Subject to any disclaimer, the term of this patent is extended or adjusted under 35 U.S.C. 154(b) by 0 days.

(21) Appl. No.: 09/332,017

(22) Filed: Jun. 14, 1999

Related U.S. Application Data

(63) Continuation of application No. 08/912,858, filed on Aug. 19, 1997, now abandoned.

(51) Int. Cl.[7] .............................................. A61B 19/00
(52) U.S. Cl. ....................................... 604/403; 604/256
(58) Field of Search ........................... 604/264, 19, 48, 604/173, 192, 313, 902, 403, 411, 256; 128/202.28, 205.12, 205.19, 909, 911, 912; 206/363, 364, 365, 368; 433/77, 91

(56) References Cited

U.S. PATENT DOCUMENTS

| | | | | |
|---|---|---|---|---|
| 4,564,054 A | * | 1/1986 | Gustavsson | 141/329 |
| 4,662,367 A | | 5/1987 | Gore, Jr. | |
| 4,673,398 A | | 6/1987 | Turner et al. | |
| 5,201,654 A | * | 4/1993 | Kuehn et al. | 433/25 |
| 5,279,576 A | * | 1/1994 | Loo et al. | 604/187 |
| 5,336,193 A | * | 8/1994 | Rom et al. | 604/171 |
| 5,676,136 A | * | 10/1997 | Russo | 128/205.24 |
| 5,874,296 A | * | 2/1999 | Kang | 435/283.1 |
| 5,925,029 A | * | 7/1999 | Jansen et al. | 604/411 |

* cited by examiner

*Primary Examiner*—Anhtuan T. Nguyen
*Assistant Examiner*—Ann Y. Lam
(74) *Attorney, Agent, or Firm*—Patula & Associates P.C.

(57) ABSTRACT

A suction device system comprising a suction tip and a containing unit wherein the containing unit is configured to allow the suction tip to rest within the containing unit such that the suction tip does not contact the containing unit.

9 Claims, 2 Drawing Sheets

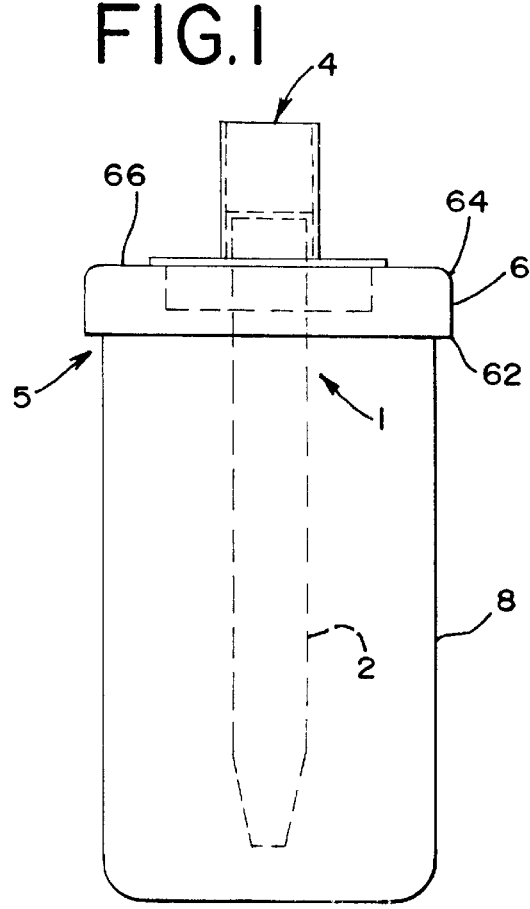
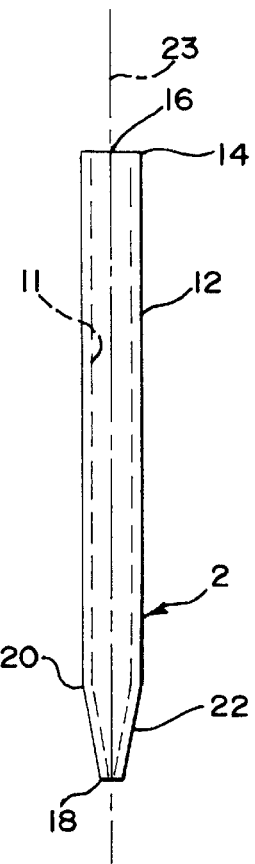
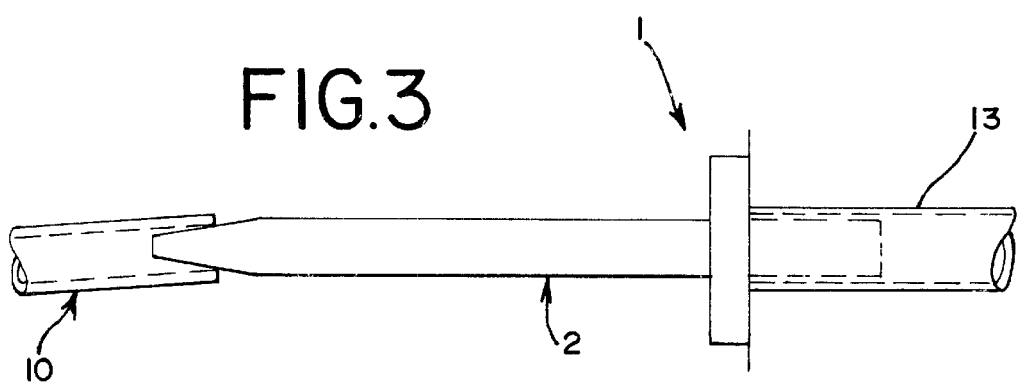

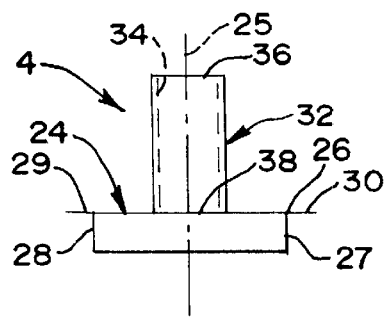
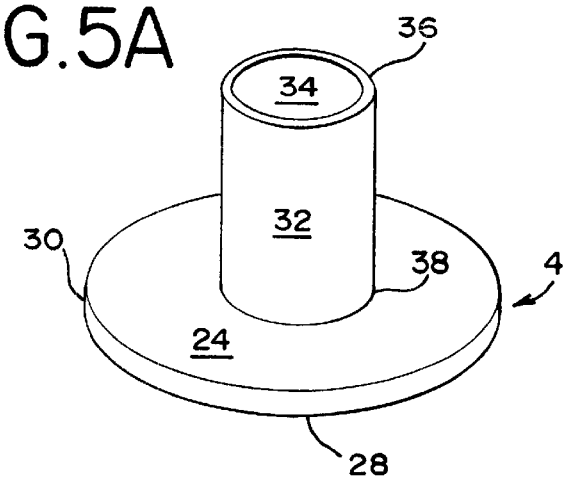
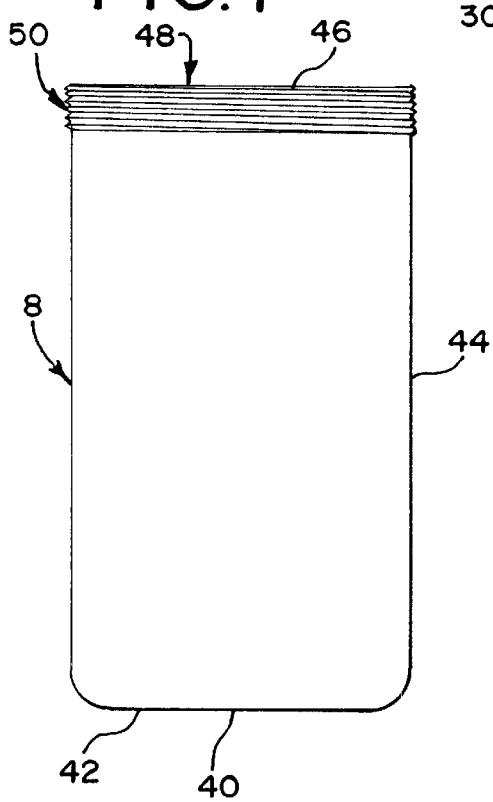
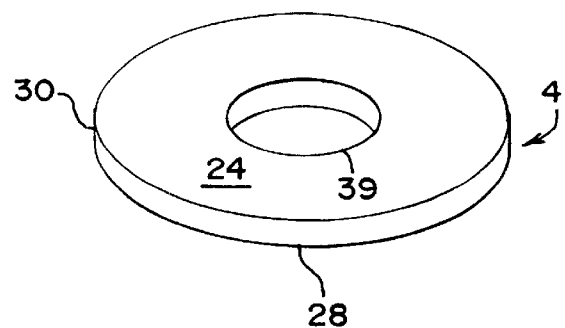
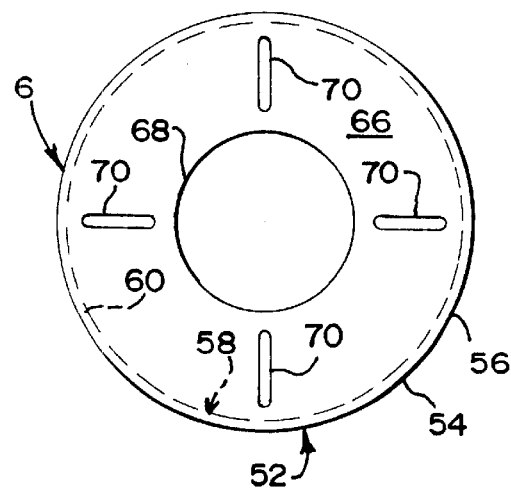

SUCTION DEVICE

This Application is a Continuation Application of U.S. Utility application, Ser. No. 08/912,858, filed with the U.S. Patent Office on Aug. 19, 1997, now abandoned.

BACKGROUND OF THE INVENTION

1. Field of the Invention

The present invention relates generally to medical and/or health care devices, and in particular to a suction device for clearing of tracheostomy tubes and the like and a sanitary container therefor.

The present invention provides a suction tip and a sanitary container for storing the same such that repeated, efficient clearing of tracheostomy tubes may be accomplished with a single suction tip without allowing substantial bacterial growth between each use thereof.

2. Description of the Related Art

The invention relates generally to a suction device employable for clearing a tracheostomy tube in a patient. A tracheostomy tube is a tube inserted through the outer surface of the body and into the trachea of patients to remedy various conditions. For instance, persons may experience blockage of the upper trachea or upper respiratory tract causing difficulty with, or a complete inability to, breathe and/or respirate. Such blockage may result from a variety of conditions or ailments. The tracheostomy tube is employed to create a bypass of the blockage and allow breathing and/or respiration through the tracheostomy tube. Tracheostomy tubes have also been employed to breakup and remove congestion in the lungs or upper respiratory tract. This may be accomplished by introducing an agent into the congested area through the tracheostomy tube to loosen the congestion. Once loosened, the congesting material may be removed from the lungs or respiratory tract by suction through the tracheostomy tube.

Regardless of the purpose for which a tracheostomy tube is installed into a patient, mucus and other bodily substances typically collect around and in the tracheostomy tube which is positioned inside the trachea of the patient. These bodily substances create difficulty or complete inability to alleviate the problems or ailments for which the tracheostomy tube is intended. It has therefore been found that periodic removal of the bodily substances which collect in and around the tube is necessary.

Removal of bodily substances which collect in and around the tracheostomy tube is preferentially accomplished without removal of the tracheostomy tube from the patient. It has been found that use of suction provides a quick and efficient manner of clearing a tracheostomy tube. However, problems exist with prior equipment for introducing suction to the tracheostomy tube. For various reasons, prior art suction devices are employable for a limited number of uses. For example, the design of many suction devices are inherently weak in construction such that the device breaks after one or two uses. Another problem exists with previous suction devices in that no means is currently available for storing such a suction device between uses which will prevent contamination of the suction device until it is desired for subsequent use. Instead, such devices are set adjacent to the patient in a manner which allows the suction tip to contact a surface on which it is laid. This contact of the suction tip promotes the growth of bacteria on the suction tip, thus promoting infection within the trachea. Therefore, because bacteria on the suction tip renders the suction tip unusable, prior suction devices were relegated to a single use before being disposed.

A tracheostomy suction device which could be used repeatedly for periodic removal of mucus and other bodily matter which collects in and around the tracheostomy tube would present many advantages over prior suction devices. The cost of manufacturing, packaging, inventorying and allocating to patients the additional suction devices required for the multiple tracheostomy tube clearings experienced by many patients would be alleviated. Additionally, the cost required for a health care professional to locate a new suction device, open and attach that device to a suction means, a cost which may become substantial over a number of tracheostomy tube clearings, would be alleviated. Elimination of the time required to locate, open and attach a new suction device also greatly reduces the risk of damage to the health of a patient experiencing a difficulty or inability to breathe. Cost savings are also experienced from a decrease in disposal costs which are ever increasing as the amount of land which can accommodate such disposals decreases.

U.S. Pat. No. 4,673,398 to Turner et al. discloses a prior attempt at a medical suction device designed for clearing of a trachea through the oral cavity by applying suction from a human being. No tracheostomy tube clearing device is taught by Turner et al. Neither does Turner et al. teach a container for storing a suction device between uses such that bacteria and other unwanted substances may attach to the device. Multiple sanitary uses of the Turner et al. device is not therefore taught.

U.S. Pat. No. 4,662,367 to Core, Jr. also discloses a prior attempt at a medical suction device which merely presents a bulbous interface between a suction source and a tracheostomy tube. No sanitary container is employed for storage between uses. Multiple sanitary uses of the Gore, Jr. device is not therefore taught.

Additionally, Children's Medical Ventures, Inc. produces a product labeled a BBG Nasal Aspirator for clearing of the nasal passages of a patient. No sanitary container is employed to prevent unwanted bacteria from attaching to the device and subsequently being introduced into the patient. Multiple sanitary uses of the BBG Nasal Aspirator device is not therefore taught. Additionally, the BBG Nasal Aspirator requires a health care professional to regulate the amount of suction delivered to the patient by adjusting the coverage of the by-pass hole. As health care professionals typically wear latex gloves over the fingers used to cover the by-pass hole, said latex tends to be suctioned into the by-pass hole even when the health care professional attempts to uncover the by-pass hole. Consequently, problems with control of the BBG Nasal Aspirator are prevalent.

It is therefore an object of the present invention to provide a medical suction device which is of durable construction and designed to allow for multiple uses thereof.

It is a further object of the present invention to provide a medical suction device which may be quickly employed.

It is a further object of the present invention to provide a medical suction device with a means of storing said medical suction device which will keep said medical suction device clean between uses.

It is a further object of the present invention to provide a medical suction device which allows a health care professional proper control over the suction provided to the application.

It is a further object of the present invention to provide a medical suction device which limits the interaction of a health care professional with tracheal secretions of a patient.

It is a further object of the present invention to provide a container that can be easily attached to a patient's bed or bedside, or placed within a portable suction bag of a patient in the home setting.

It is a further object of the present invention to provide an acutely tapered suction tip to easily grasp tracheal secretions deep within the external protrudence of the tracheostomy tube.

It is a further object of the present invention to provide a vented storage container to avoid bacterial growth within said container.

SUMMARY OF THE INVENTION

The above and other objects of the present invention are accomplished by providing a suction device employable for clearing a tracheostomy tube, said suction device comprising a suction tip configured to be inserted into a sanitary adapter which allows for an air tight connection to a suction means. The suction tip is comprised of an elongated tube with a nozzle at an end distal from the sanitary adapter and a lip at the end proximate the sanitary adapter to provide an air tight force fit between the suction tube and the sanitary adapter. The sanitary adapter comprises an adapter tip extending therefrom, which is configured as a tube for accepting the suction tip therein and a suction means there over. In this manner, suction provided by a suction means may be directed through the sanitary adapter to the nozzle of the suction tip.

The suction tip of the present invention is configured to rest in a sanitary container which is covered by a sanitary lid. The sanitary container resembles a jar with a base at a first end thereof and threads at the opposing end thereof to allow securing of the sanitary lid thereon. The sanitary lid comprises threads which complement those of the sanitary container. The sanitary lid further comprises an adapter port to allow the insertion of the suction tip and a portion of the sanitary adapter therein. The sanitary adapter comprises a locator lip and a suspension lip. The locator lip positions the sanitary adapter laterally with respect to said adapter port. The perimeter of the suspension lip is designed to be larger than the perimeter of the adapter port such that the suspension lip stops progression of the sanitary adapter into the adapter port. The top of the threads of the sanitary container are configured at a distance from the base thereof which is greater than the distance from the suspension lip of the sanitary adapter to the nozzle of the suction tip when the suction tip is inserted into the sanitary adapter in the manner required to provide a snug fit. The sanitary lid may also have air holes or vents therein to avoid bacterial growth on the suction tip in the sanitary container which would be fostered by still air therein.

In this configuration, the suction tip of the present invention may be employed to clear the tracheostomy tube of a patient and then placed into the sanitary container through the adapter port of the sanitary lid without the suction tip contacting any objects. Additionally, the present suction tip may be stored without contacting any objects, until the patient again needs clearing of the tracheostomy tube. Because the suction tip contacts no object between uses thereof, the introduction of bacteria to the suction tip, and therefore the patient, is reduced or eliminated.

Numerous other advantages and features of the invention will become readily apparent from the detailed description of the preferred embodiment of the invention, from the claims, and from the accompanying drawings, in which like numerals are employed to designate like parts throughout the same.

BRIEF DESCRIPTION OF THE DRAWINGS

A fuller understanding of the foregoing may be had by reference to the accompanying drawings, wherein:

FIG. 1 is a substantially schematic side view of the suction device of the present invention.

FIG. 2 is a substantially schematic side view of the suction tip of the present invention.

FIG. 3 is a substantially schematic side view of the suction tip of the present invention positioned at a tracheostomy tube in a preferred manner for suction of said tracheostomy tube.

FIG. 4 is a substantially schematic side view of the sanitary adapter of the present invention.

FIG. 5A is a substantially schematic perspective view of the preferred sanitary adapter of the present invention.

FIG. 5B is a substantially schematic perspective view of an alternative sanitary adapter of the present invention.

FIG. 6 is a substantially schematic side view of the sanitary container lid of the present invention.

FIG. 7 is a substantially schematic side view of the sanitary container of the present invention.

DETAILED DESCRIPTION OF THE PREFERRED EMBODIMENTS

While the invention is susceptible of embodiment in many different forms there is shown in the drawings and will be described herein in detail, a preferred embodiment of the invention. It should be understood, however, that the present disclosure is to be considered an exemplification of the principles of the invention and is not intended to limit the spirit and scope of the invention and/or claims of the embodiment illustrated.

As depicted in FIG. 1, the suction device 1 of the present invention comprises a suction tip 2 fitted into a sanitary adapter 4, stored in a container unit 5 preferably comprising a sanitary container lid 6 and a sanitary container 8. The suction device 1 is designed to allow efficient and safe removal of bodily matter from a tracheostomy tube 10 (FIG. 3) which has been inserted into the trachea (not shown) of a patient's respiratory system.

The suction tip 2, depicted in FIG. 2, consists of an elongated hollow tube comprising an internal passageway 11 and suction tip exterior 12 to provide a sanitary extension of a suction means 13 (FIG. 3). The suction tip 2 comprises a lip 14 located around the perimeter of a first end 16 of the suction tip 2 which opposes a nozzle 22 at a second end 18 of the suction tip 2. The suction tip 2 is preferably, although not necessarily, of a uniform diameter between the lip 14 and a position 20 located intermediate of the lip 14 and the suction tip second end 18. The perimeter of the suction tip narrows from the position 20 toward the second end 18, preferably in a conical manner, to form the nozzle 22. By making the outer diameter of the nozzle 22 smaller than the inner diameter of the standard tracheostomy tube 10, a health care professional using the suction device 1 may quickly and efficiently locate the suction tip 2 in the tracheostomy tube 10 which is in need of clearing as depicted in FIG. 3. While the conical nozzle depicted in FIGS. 1 and 2 is preferred, other nozzles 22 as are known in the art are contemplated as well. Specifically, it is contemplated that the distance between the position 20 and the second end 18 is great enough so that comprising the narrowing perimeter therebetween of an acute taper would allow the second end 18 to extend deep within the tracheostomy tube to grasp tracheal secretions therein.

While varying dimensions of the suction tip 2 of the present invention are contemplated, some specific dimensions have been found to provide optimum performance. In a preferred embodiment suction tip 2 employs a circular cross-section having an outer diameter as measured at the suction tip exterior 12 adjacent to the lip 14. The outer diameter of suction tip 2 preferably measures 0.8 centimeters. The outer diameter at the second end 18 of the suction tip 2 preferably measures 0.5 centimeters. The preferable length of the suction tip 2 as measured from the first end 16 to the second end 18 along a longitude axis 23 measures 9.0 centimeters. Although the suction tip 2 as described above represents the preferred suction tip 2 of the present invention, it should be noted that other configurations are contemplated such that the second end 18 of the suction tip 2 may be properly inserted into the tracheostomy tube 10 and remove blockages therefrom as depicted in FIG. 3 consistent with the present invention. Furthermore, while the suction tip 2 is depicted as having a circular cross-section or exterior 12, other shaped exteriors 12 are contemplated. Likewise, sanitary adapter 4, sanitary container lid 6 and sanitary container 8 may be of other shapes not shown.

Sanitary adapter 4 is configured to accept suction tip 2 of the present invention therein to form said suction device 1. The sanitary adaptor 4 comprises a longitudinal axis 25 which aligns with longitudinal axis 23 of said suction tip 2. As best seen in FIGS. 4 and 5 sanitary adapter 4 preferably comprises a base area 24 having a perimeter 26 and a ring-like locator extension 27 extending from a bottom of the perimeter 26 of the base area for locating said sanitary adapter 4 into the sanitary container lid 6. The locator extension 27 is preferably placed around substantially the entire periphery 26 of the base 24 to form a locator lip 28 as depicted in FIGS. 1,3,4 and 5.

Alternatively, the locator extension 27 could take the form of at least one tab-like extension depending from the perimeter 26 of the base 24. Said locator extension preferably, although not necessarily, extends substantially parallel to said sanitary adaptor longitudinal axis 25. Although said at least one locator extension 27 preferably extends parallel to said sanitary adaptor longitudinal axis, it is contemplated that angling the locator extension 27 inward from said perimeter 26 would allow easy location of said sanitary adaptor 4 to said sanitary container lid 6.

Sanitary adapter 4 further comprises a suspension extension 29 extending substantially perpendicular to, and outward of, the sanitary adaptor longitudinal axis 25 from said perimeter 26 of said base 24 to allow the sanitary adapter 4 to be suspended from the sanitary container lid 6. The suspension extension 29 is preferably placed around substantially the entire perimeter 26 of the base 24 to form a suspension lip 30 as depicted in FIGS. 1, 3, 4 and 5. Alternatively, the suspension extension 29 could take the form of at least two tab-like extensions.

Sanitary adapter 4 further comprises an adapter tip 32 extending from the top of the base area 24 and substantially parallel to the longitudinal axis 25 of the adapter 4. The adapter tip 32 of the sanitary adapter 4 comprises a hollow tube having an internal passage 34 which extends from a first end 36 of the adapter tip 32 to an opposing second end 38 of the adapter tip 32.

The internal passage 34 of the sanitary adapter 4 is configured to accept the suction tip 2 therein as depicted in FIGS. 1 and 3. The diameter of the internal passage 34 of the sanitary adapter 4 is configured to be at least substantially the same as the diameter of the suction tip exterior 12 such that suction applied to the first end 36 of the adapter tip 32 will be experienced at the nozzle 22 of the suction tip 2 without substantial losses of suction due to seepage between the suction tip 2 and the internal passage 34 of the sanitary adapter 4. To insure that seepage is either eliminated or kept to a minimum, the lip 14 of the suction tip 2 is preferably configured to be of a greater diameter than the internal passage 34 of the sanitary adapter 4 to produce a forced fit therebetween. It is contemplated, however, that proper suction may be achieved at the suction tip 2 without the lip 14. Other means known in the art of securing a tight fit between the suction tip 2 and the sanitary adapter 4 are contemplated.

The adapter tip 32 is configured to be inserted into a suction tube 13 as depicted in FIG. 3. To provide quick and easy insertion of the first end 36 of the adapter tip 32 into a suction tube 13, the outer diameter of the adapter tip first end 36 is preferably of a diameter smaller than the inner diameter of the suction tube 13. Again, a forced fit is desired between the adapter tip 32 and the suction tube 13 to ensure a transfer of suction without losses due to seepage. A slight taper is therefore preferably created from a smaller diameter at the first end 36 to a larger diameter at the second end 38. In this manner, the outer diameter of the adapter tip 32 at the second end 38 can be a greater diameter than the inner diameter of the suction tube 13 and a forced fit is accomplished between the adapter tip 32 and the suction tube 13. To allow an individual to quickly place a suction tube 13 over the adapter tip 32, the taper from the adapter tip first end 36 to the second end 38 must be gradual. It has been found that a length of 2.0 centimeters from the adapter tip first end 36 to the adapter tip second end 38 provides sufficient distance over which a suction tube 13 may be force fitted onto the adapter tip 32 of the present invention with a taper gradual enough that an ordinary health care professional may easily accomplish the desired forced fit. Other means of creating a force fit, consistent with those known in the art, are contemplated for use between the adapter 4 and the suction tube 13.

In an alternative embodiment, depicted in FIG. 5B, the adapter tip 32 is eliminated from the sanitary adapter 4 leaving sanitary adapter port 39 in the sanitary adapter base area 24.

The diameter of the adapter port 39 is configured such that the suction tip 2 is inserted therein to provide a force fit between the sanitary adapter 4 and the suction tip 2. The suction tube 13 may then simply be placed over the suction tip first end 16 to provide the required suction at the suction tip nozzle 22. In another alternative embodiment (not depicted), the suction tip 2 and the sanitary adapter 4 may be integrally formed as a single piece.

The sanitary container 8, as depicted in FIGS. 1 and 7, preferably comprises a jar type container having a base 40 at a first end 42 thereof and an enclosure wall 44 extending around the periphery of the base 40 substantially perpendicular thereto and forming an enclosure with a circular opening 46 at the second end 48 of the sanitary container 8. While it is preferred that the enclosure wall 44 extend substantially perpendicular to the base 40 to keep manufacturing costs at a minimum, other angles are contemplated. The second end 48 of the sanitary container 8 further comprises threads 50 preferably, although not necessarily, extending around the exterior of the enclosure wall 44 from the second end 48 of the sanitary container 8 to a position between the first and second end 42,48 of the sanitary container 8. To assure that the suction tip 2 does not contact the container 8, enclosure wall 44 preferably extends from the base 40 to a distance which is at least substantially equal to the length of the suction tip 2 as measured from the first end 16 thereof to the second end 18 thereof. However, because insertion of the suction tip 2 into the sanitary adapter 4 will distance the suction tip second end 18 from the base 40 of the container 8, contact between the suction tip 2 and the container 8 may be avoided with an enclosure wall 44 of lesser length. The diameter of the base 40, and consequently the diameter of the enclosure wall 44, is preferably great enough that the suction tip 2 may be inserted into the sanitary container 8 without the suction tip 2 contacting the enclosure wall 44 of the sanitary container 8 and yet not requiring great care of the health care worker performing that task. Although other dimensions are contemplated, it has been found that a diameter of 5.0 centimeters for the base 40 and the enclosure wall 44 will accomplish this objective sufficiently. Furthermore, while the threaded connection between the sanitary container 8 and the sanitary container lid 6 is preferred, other means of accomplishing a tight connection therebetween are contemplated.

As depicted in FIGS. 1 and 6, the sanitary lid 6 provides a partial closure of the sanitary container second end 48. The sanitary lid 6 comprises a circumferential wall 52. A circumferential wall exterior 54 is comprised of a pattern of indentations or raised portions 56 (not depicted) to provide a user of the present suction tip 2 with a proper grip of the circumferential wall exterior 54. Any pattern of indentations or raised portions 56 known in the art would suffice to allow a user said proper grip. The circumferential wall interior 58 comprises threads 60 which complement, and are designed to mesh with, the threads 50 of the sanitary container 8. It is contemplated, however, that instead of threads, the lid could be fastened to the container 8 in any manner known in the art.

The area encompassed by a first end 62 of the circumferential wall 52 of the sanitary lid 6 is left unobstructed to allow placement over the sanitary container 8. The area encompassed by a second end 64 of the circumferential wall is partially enclosed by a second end wall 66 extending over and between the circumferential wall second end 64 and having an adapter port 68 preferably located centrally therein. The adapter port 68 is large enough to accept the locator lip 28 of the sanitary adapter 4 without great care of locating the sanitary adapter 4 with respect to the adapter port 68. However, the diameter of the suspension lip 30 of the sanitary adapter 4 is greater than the diameter of the adapter port 68 such that the locator lip 28 of the sanitary adapter 4 and an attached suction tip 2 may be placed into the adapter port 68 while an adapter tip 32 and attached suction tube 13 may remain outside of the adapter port 68 as depicted in FIG. 1. Therefore, the suspension lip 30 preferably extends outward of the locator lip 28 a distance which will allow easy insertion of the sanitary adapter 4 into the sanitary lid 6 while providing enough overlap with the second end wall 66 to ensure that the sanitary adapter 4 does not pass through the adapter port 68 of the sanitary lid 6.

In order to avoid sealing the inside of the sanitary container 8 from external air, the sanitary lid 6 preferably has at least one vent hole 70 located therein. The vent hole 70 allows flow of air into and out of the sanitary container 8 so a that the sanitary container 8 does not surround the adapter tip 2 with a stagnant air body which would promote the growth of bacteria. It is contemplated that the at least one vent hole 70 could alternatively, or in supplement, be located on the sanitary container 8 or the sanitary adapter 4.

In an alternative embodiment, the sanitary container 8 and the sanitary container lid 6 may be accomplished by a single piece containing unit (not shown) rather than the preferred two piece assembly depicted in FIG. 1. It is even contemplated that the sanitary container 8 as depicted in FIG. 7 may by itself accomplish such a single piece containing unit when the suspension lip 30 of the sanitary adapter 4 is large enough to accomplish suspension of the sanitary adapter 4 in such a containing unit.

In use, the suction tip 2 of the present invention is force fitted into the sanitary adapter 4 which in turn is force fitted into the suction tube 13 which is in turn connected to a suction machine (not depicted). Furthermore, the sanitary lid 6 is threaded onto the sanitary container 8 and tightened thereon. The suction tip 2 may then be used as needed to clean a tracheostomy tube 10 of a designated patient associated with the suction tip 2 as depicted generally in FIG. 3. To use the present suction tip 2 a health care professional simply grasps the suction tube 13 and removes the sanitary adapter 4 and the suction tip 2 from the sanitary container 8 through the adapter port 68 of the sanitary lid 6. It is preferred that a health care professional grasp the suction tube 13 as close to the sanitary adapter base area 24 as possible to increase the force between the suction tube 13 and the adapter tip 32. This helps prevent loss of suction at the connection between the suction tube 13 and the adapter tip 32.

Once clearing of the tracheostomy tube 10 is accomplished, the suction tip 2 and the locator lip 28 are reinserted into the sanitary container 8 through the adapter port 68 for sanitary storage. As depicted in FIG. 1, the suction tip 2 of the present invention contacts only the internal passage 34 of the adapter tip 32 at the first end 16 of the suction tip 2. The locator lip 28 locates the sanitary adapter 4 and the suction tip 2 such that the suction tip makes no contact with the sanitary container 8 or the sanitary lid 6 when in sanitary storage.

Further, it is contemplated that the sanitary container 8 may hold any known disinfectant. In this manner, the suction tip 2 may be disinfected while resting in the sanitary container.

The foregoing specification describes only the preferred embodiment of the invention as shown. Other embodiments besides those presented above may be articulated as well. For example, the container 8 could be suitably fastened or held to any object such as the suction means. Alternatively, the container 8 could be an integral chamber of any object such as the suction means. Also, the container 8 could be oriented in any manner such that the suction tip 2 could be inserted at any angle or from the side, etc. The terms and expressions used in the foregoing specification serve only to describe the invention by example only and not to limit the invention. It is expected that others will perceive differences which while differing from the foregoing, do not depart from the spirit and scope of the invention herein described and claimed.

We claim:

1. A suction device system comprising:
    an acutely tapered suction tip;
    a containing unit removably receiving said suction tips, wherein said containing unit is configured to allow said suction tip to rest within said containing unit such that said suction tip does not contact either said containing unit or liquid contained by said containing unit and wherein, said suction device system configured to allow passage of gases or fluids into and out of the containing unit when said suction tip rests within said containing unit; and
    an adapter releasably connected to said suction tip, said adapter comprising a periphery and at least two suspension extensions extending from said periphery outwardly from said suction tip, said adapter being unconnected to said container or any lid attached to said container;

wherein said container unit comprises a container and a lid releasably attached to said container, wherein the passage of gases or fluids is afforded by said suction device having said adapter port located in said lid and configured to allow said suction tip to pass therethrough and said container unit having at least one vent hole located in at least one of said lid and said container.

2. The suction device system of claim 1, wherein said containing unit having an adapter port located therein and said adapter port is configured to allow passage of said suction tip therethrough.

3. The suction device system of claim 2, wherein said at least two suspension extensions being of a length such that said at least two suspension extensions obstruct the passage of said adapter through said adapter port.

4. The suction device system of claim 3, wherein said at least two suspension extensions form a suspension lip extending around substantially the entire periphery of said adapter.

5. The suction device system of claim 3, wherein said adapter further comprises at least one locator extension extending from said adapter to locate said adapter within said adapter port and said suction tip within said container such that said suction tip does not contact said container.

6. The suction device system of claim 1, wherein said suction tip comprising a first end, a second end and an outer diameter, said first end comprising a lip extending outward of the outer diameter to allow a force fit connection with said adapter, said second end comprising a nozzle.

7. A storage system for a suction device comprising:
   a container unit having an adapter port located therein; and
   an adapter configured to removably accept a suction tip therein, said adapter further configured to allow said suction tip to rest in said container unit without contacting said container unit and wherein said storage system is configured to allow passage of gases or fluids into and out of the containing unit when said suction tip rests within said containing unit, said adapter comprising a periphery and at least two suspension extensions extending from said periphery to obstruct the passage of said adapter through said adapter hole;
   wherein said at least two suspension extensions form a suspension lip extending around substantially the entire periphery of said adapter;
   wherein said container unit comprises a container and a lid releasably attachable to said container, said container unit having said adapter port located in said lid and wherein the passage of gases or fluids in and out of said container is afforded by said container unit having at least one vent hole located in at least one of said lid and said container.

8. The storage system for a suction device of claim 7, wherein said adapter further comprises at least one locator extension extending from said adapter to locate said adapter within said adapter port and said suction tip within said container such that said suction tip does not contact said container.

9. A sanitary suction device system for allowing repeated, efficient clearing of a tracheostomy tube while preventing substantial bacterial growth between uses, said system comprising:
   a tubular suction member having a first end and a second end, said first end having a nozzle being adapted to engage said tracheostomy tube;
   a sanitary adapter attached to said second end of said tubular suction member, said adaptor comprising a tubular portion and a base portion, said tubular portion receiving said tubular suction member at one end, said base portion comprising a disk-like member extending radially out from said tubular portion, and having a ring-like member depending therefrom, said base portion further comprising at least one suspension element extending outward from a perimeter of said disk-like member, said tubular portion of said adaptor being configured to attach to a suction tube at an opposite end from where said tubular suction member is attached;
   a container; and
   a container lid affixed to said container, said container lid including at least one vent hole allowing for the passage of gases into and out of said container, said container lid further including an adaptor port therein, said adaptor port being configured to allow insertion of said tubular suction member and said ring-like member therethrough, while preventing the passage of said at least one suspension element therethrough, wherein said container lid removably supports said adaptor and in turn said tubular suction member attached to said adaptor in such a manner as to prevent contact between said tubular suction member and said container and any foreign object so as to substantially prevent bacterial growth on said tubular suction member.

* * * * *